US008883889B2

(12) United States Patent
Ruffieux et al.

(10) Patent No.: US 8,883,889 B2
(45) Date of Patent: Nov. 11, 2014

(54) PIGMENT COMPOSITIONS COMPRISING PYRROLO[3,4-C]PYRROLES

(75) Inventors: Vincent Ruffieux, Marly (CH); Florence Modoux, Basel (CH)

(73) Assignee: BASF SE, Ludwigshafen (DE)

( * ) Notice: Subject to any disclaimer, the term of this patent is extended or adjusted under 35 U.S.C. 154(b) by 1147 days.

(21) Appl. No.: 11/654,154

(22) Filed: Jan. 17, 2007

(65) Prior Publication Data
US 2007/0117889 A1    May 24, 2007

Related U.S. Application Data

(62) Division of application No. 10/489,037, filed as application No. PCT/EP02/09791 on Sep. 3, 2002, now Pat. No. 7,186,847.

(30) Foreign Application Priority Data

Sep. 11, 2001  (EP) ..................................... 01810875
Dec. 20, 2001  (EP) ..................................... 01811249
Mar. 22, 2002  (EP) ..................................... 02405223

(51) Int. Cl.
C08K 5/34      (2006.01)
C07D 487/02    (2006.01)
C09B 57/00     (2006.01)
C09K 11/06     (2006.01)
C07D 487/04    (2006.01)
C09B 67/22     (2006.01)
C07D 491/04    (2006.01)

(52) U.S. Cl.
CPC ...... *C07D 487/04* (2013.01); *G09K 2211/1011* (2013.01); *C09B 57/004* (2013.01); *C09K 11/06* (2013.01); *C09K 2211/1044* (2013.01); *C09B 67/0039* (2013.01); *C07D 491/04* (2013.01); *C09K 2211/1033* (2013.01)
USPC ............................................. 524/94; 548/453

(58) Field of Classification Search
CPC ........................... C09B 67/0039; C09B 57/004
See application file for complete search history.

(56) References Cited

U.S. PATENT DOCUMENTS

| | | | |
|---|---|---|---|
| 4,579,949 A | 4/1986 | Rochat et al. | 546/167 |
| 4,585,878 A | 4/1986 | Jost et al. | 548/453 |
| 4,783,540 A * | 11/1988 | Babler | 548/453 |
| 5,200,528 A | 4/1993 | Wooden et al. | 548/453 |
| 5,354,869 A | 10/1994 | Langhals et al. | |
| 5,424,157 A | 6/1995 | Miyamoto et al. | 430/73 |
| 5,476,949 A | 12/1995 | Wallquist et al. | 548/453 |
| 5,646,299 A | 7/1997 | Hao et al. | 548/453 |
| 5,738,719 A | 4/1998 | Wallquist et al. | 106/498 |
| 5,847,156 A | 12/1998 | Eldin et al. | 548/453 |
| 6,048,918 A | 4/2000 | Eldin et al. | |
| 6,057,449 A | 5/2000 | Hendi | 546/276.7 |
| 6,066,202 A | 5/2000 | Wallquist et al. | |
| 6,361,594 B1 | 3/2002 | Hendi | 106/498 |
| 6,566,519 B2 | 5/2003 | Nickel et al. | 544/336 |
| 2003/0089280 A1 | 5/2003 | Lenz et al. | |

FOREIGN PATENT DOCUMENTS

| | | |
|---|---|---|
| EP | 0640602 | 3/1995 |
| EP | 1087005 A1 | 3/2001 |
| EP | 1087006 A1 | 3/2001 |
| WO | 96/08537 | 3/1996 |
| WO | 03/014255 | 2/2003 |

OTHER PUBLICATIONS

Langhals et al., Liebigs Annalen Organischen Bioorganischen Chemie, vol. 5, (1996), pp. 679-682.
Peter Edman et al., The Journal of Physical Chemistry, (Mar. 1995), vol. 99, pp. 8504-8509.
Jost, et al., "The Synthesis and Properties of 1,4-Diketo-Pyrrolo[3,4-C]Pyrroles", Bull. Soc. Chim. Belg., 97, No. 8-9: 615-643 (1988).
Zambounis, et al., "Latent pigments activated by heat", Nature, 388: 131-132 (1997).
International Search Report mailed Nov. 21, 2002 for PCT/EP02/09791.
International Preliminary Examination Report completed Jun. 11, 2003 for PCT/EP02/09791.

* cited by examiner

*Primary Examiner* — Kortney L Klinkel
(74) *Attorney, Agent, or Firm* — Drinker Biddle & Reath

(57) ABSTRACT

The present invention relates to a process for the direct preparation of pyrrolo[3,4-c]pyrroles (DPPs) of the formula

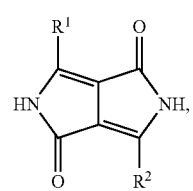
(I)

pigment compositions containing them and their use for coloring high molecular weight organic materials, such as plastics and paints. The obtained DPPs of the formula I possess a higher color strength, a higher chroma, a purer shade and a higher opacity versus corresponding commercially available DPPs.

10 Claims, No Drawings

PIGMENT COMPOSITIONS COMPRISING PYRROLO[3,4-C]PYRROLES

This is a divisional of U.S. application Ser. No. 10/489,037 filed Mar. 5, 2004 now U.S. Pat. No. 7,186,847, filed as Application No. PCT/EP02/09791 on Sep. 30, 2002.

The present invention relates to a process for the direct preparation of pyrrolo[3,4-c]pyrroles (DPPs) of the formula (I), pigment compositions containing them and their use for coloring high molecular weight organic materials, such as plastics (including Engineering PoLymers (EPL)) and paints. The obtained DPPs of the formula I possess a higher colour strength, a higher chroma, a purer shade and a higher opacity versus corresponding commercially available DPPs.

It is known in the pigments art that substituted diketopyrrolopyrrole pigments can be prepared by the reaction of a mole of a disuccinate with two moles of an aromatic nitrile or one mole each of two different aromatic nitrites. U.S. Pat. No. 4,579,949 describes reaction of a disuccinate with aromatic nitrites in an organic solvent and in the presence of a strong base at elevated temperature, and subsequently protolyzing the resultant salt. The product of such process, known as crude diketopyrrolopyrrole, generally has a medium to large particle size. It is necessary to further process the larger particle size crude pigments to obtain the desired pigment properties, such as particle size, particle size distribution, particle shape or polymorphic phase.

Particle size manipulation has thus become a significant art in pigment technology. Highly desirable pigments are traditionally produced by subjecting the crude pigments to a variety of pigment finishing methods, also called pigment conditioning steps, the purpose of which is to create pigments of defined particle size with a narrower particle size distribution, preferably in a single homogeneous crystal phase. In the case of diketopyrrolopyrroles opaque forms are commonly obtained by direct ripening of the protolysed pigment in a mixture of water and miscible solvent at elevated temperature, or by crystallisation in organic solvents or organic solvent mixtures. Mechanical treatment like salt kneading in the presence of aprotic solvents is also suitable to obtain opaque DPP pigments.

EP-A-640 602 und EP-A-640 603 describe that certain cyano-substituted diketopyrrolo-pyrrole pigments can be prepared in finely particulate form by carrying out the protonation step in water and/or an alcohol in the presence of an acid in an amount sufficient to keep the pH less than 9, and a temperature of greater than 90° C. Inclusion of particle growth regulators during the synthesis of diketopyrrolopyrroles is not mentioned.

U.S. Pat. No. 5,738,719 describes that when a minor amount of a cyano-substituted diketopyrrolo-pyrrole is added before or during the synthesis of a pyrrolopyrrole which is not substituted by cyano, the crystal growth inhibition is very surprisingly enhanced. Accordingly it is possible to produce, depending on the conditions of protolysis, highly transparent as well as opaque pigment forms of superior colour strength which are particularly resistant to recrystallisation and heat and which are also very suitable for the warp-free pigmenting of polyolefins.

U.S. Pat. No. 6,057,449 discloses a process for the direct preparation of transparent pigmentary 1,4-diketopyrrolo-[3,4-c]pyrroles of the formula (I)

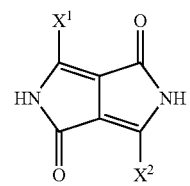

wherein each of $X^1$ and $X^2$ independently of the other is an isocyclic or heterocyclic aromatic radical, which process comprises heating an appropriate molar ratio of a disuccinate with a nitrile of the formula (II)

$$X^1\text{—CN} \tag{II}$$

or of the formula (III)

$$X^2\text{—CN} \tag{III}$$

or with mixtures of said nitrites, in an organic solvent and in the presence of a strong base and an effective amount of selected particle growth inhibitors, and then obtaining the compound of formula (I) from the reaction product by protolysis.

The object of the present invention is to provide a process for the direct preparation of opaque pigmentary diketopyrrolopyrroles having a narrower particle size distribution, a higher colour strength, a higher chroma, a purer shade and/or a higher opacity versus corresponding commercially available DPPs.

Said object has been solved by a process for the direct preparation of 1,4-diketopyrrolo[3,4-c]pyrroles of the formula

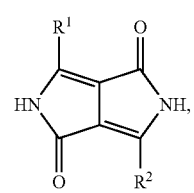

wherein $R^1$ and $R^2$ independently of each other are an unsubstituted or substituted isocyclic or heterocyclic aromatic radical, which process comprises (a) heating an appropriate molar ratio of a disuccinate with a nitrile of the formula (II)

$$R^1\text{—CN} \tag{II}$$

or of the formula (III)

$$R^2\text{—CN} \tag{III}$$

or with mixtures of said nitrites, in an organic solvent and in the presence of a strong base, to form a product, (b) conditioning of the intermediate condensation product obtained in step (a) in water or a mixture of water and a water-miscible solvent, optionally in the presence of an inorganic acid to form the compound of formula (I), and (c) optionally conditioning of the product obtained in step (b) in an aprotic solvent, characterized in that a nitrile compound of the formula

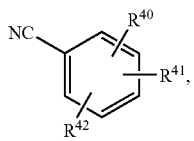

wherein $R^{40}$, $R^{41}$ and $R^{42}$ are independently of each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$ or $SO_2R^9$; is added at the beginning of the synthesis, wherein a particle growth regulator of the formula

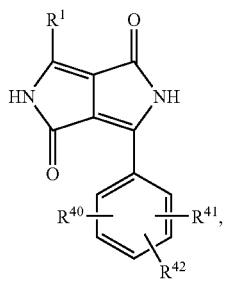

(IVa)

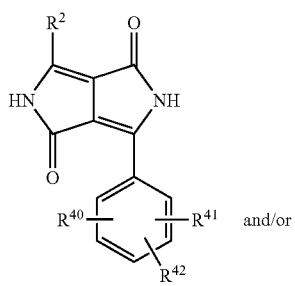

(IVb) and/or

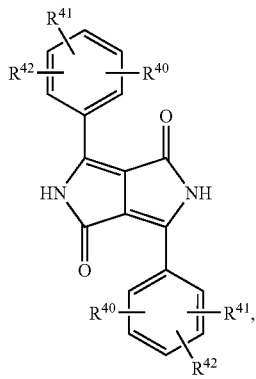

(IVc)

is obtained, wherein $R^1$, $R^2$, $R^{40}$, $R^{41}$ and $R^{42}$ are as defined above, or a particle growth regulator is added in the heating step (a), the conditioning step (b) or (c), wherein said particle growth regulator is a compound of the formula

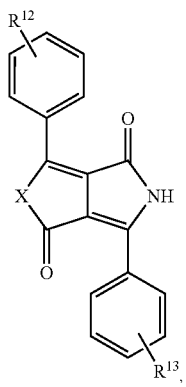

(V)

wherein X is O, S or $NR^{14}$, wherein $R^{14}$ is linear or branched $C_{1-10}$-alkyl, $C_{7-10}$-aralkyl or $C_{6-10}$-aryl; $R^{12}$ and $R^{13}$ are independently of each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$, $SO_2R^9$; or a compound of the formula

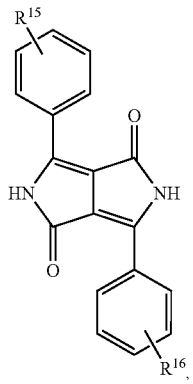

(VI)

wherein $R^{15}$ and $R^{16}$ are independently of each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$, $SO_2R^9$, wherein $R^5$ and $R^6$ are hydrogen, linear or branched $C_{1-10}$-alkyl, $C_{5-10}$-cycloalkyl or $C_{6-10}$-aryl, $R^7$ is hydrogen, linear or branched $C_{1-10}$-alkyl, $C_{5-10}$-cycloalkyl, $C_{7-10}$-aralkyl or $C_{6-10}$-aryl, $R^9$ is hydrogen, linear or branched $C_{1-10}$-alkyl, $C_{5-10}$-cycloalkyl, $C_{7-10}$-aralkyl, $C_{6-10}$-aryl or $NR^{10}R^{11}$, wherein $R^{10}$ and $R^{11}$ are hydrogen, linear or branched $C_{1-10}$-alkyl, $C_{7-10}$-aralkyl or $C_{6-10}$-aryl.

The nitrile of formula IV is different from the nitriles of formula II and III and the DPP compound of formula I is different from the DPP compound of formula VI.

$C_1$-$C_{18}$ alkyl is typically linear or branched—where possible—and examples of $C_1$-$C_{18}$ alkyl are methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl and octadecyl. $C_{1-10}$-alkyl, such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, and decyl, is preferred. $C_1$-$C_4$ alkyl such as methyl, ethyl, n-propyl, isopropyl, n-butyl, sec.-butyl, isobutyl or tert.-butyl is particularly preferred.

Examples of $C_1$-$C_{18}$alkoxy, which can be linear or branched, are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, wherein $C_1$-$C_4$ alkoxy such as methoxy, ethoxy, n-propoxy, isopropoxy, n-butoxy, sec.-butoxy, isobutoxy and tert.-butoxy is preferred.

The term "$C_{2-18}$-alkylcarbamoyl group" means a group "—C(O)—NH—$C_{1-18}$-alkyl". The term "$C_{2-18}$-alkoxycarbonyl group" means a group "—C(O)—O—$C_{1-18}$-alkyl". The term "$C_{2-18}$-alkanoylamino group" means a group "—NH—C(O)—O—$C_{1-18}$-alkyl".

The term "$C_{1-10}$-alkylthio group" means the same groups as the "$C_{1-10}$-alkoxy groups", except that the oxygen atom of ether linkage is replaced by a sulfur atom.

The term "$C_{6-10}$-aryl group" is typically phenyl, 1-naphthyl or 2-naphthyl, which may be unsubstituted or substituted. The terms "$C_{6-10}$-aryloxy group" and "$C_{6-10}$-arylthio group" means "$C_{6-10}$-aryl-O—" and "$C_{6-10}$-aryl-S—", respectively.

The term "$C_{7-10}$-aralkyl group" is typically benzyl, 2-benzyl-2-propyl, β-phenyl-ethyl or α,α-dimethylbenzyl. The terms "$C_{6-10}$-aralkyloxy group" and "$C_{6-10}$-aralkylthio group" means "$C_{6-10}$-aralkyl-O—" and "$C_{6-10}$-aralkyl-S—", respectively.

The term "$C_{5-10}$-cycloalkyl group" is typically cyclopentyl, cyclohexyl or cycloheptyl, which may be unsubstituted or substituted.

The above-mentioned substituents can be substituted by a $C_{1-8}$-alkyl, a hydroxyl group, a mercapto group, $C_1$-$C_8$ alkoxy, $C_1$-$C_8$ alkylthio, halogen, a cyano group or an amino group.

Halogen means fluorine, chlorine, bromine and iodine, preferably chlorine.

The present process provides an improvement in simplicity and economy for the preparation of a variety of opaque diketopyrrolopyrrole pigments. This approach eliminates the need for laborious conditioning processes which are currently practiced in the pigments industry for the manufacture of opaque diketopyrrolo[3,4-c]pyrrole pigments.

Due to the presence of crystal growth regulors DPP particles exhibiting a higher opacity/hiding power than commercial pigments synthesized without growth controllers are obtained. Normally, a higher opacity is connected with duller aspect, lower chroma, bluer hue (in the case of red DPP pigments) and weaker colour strength. In the present case, the shade is purer, the hue is yellowier, the chroma is considerably stronger and the colour strength is higher than or at least equal to commercial available DPP pigments.

The expressions "direct" or "directly", when used herein to describe a preparatory process for a pigmentary product, means that the specific surface area of the pigmentary product will be within the range which makes it suitable for use as a pigment with specific desired properties.

The radicals $R^1$ and $R^2$ may be the same or different, but are preferably identical. $R^1$ and $R^2$ as isocyclic aromatic radicals are preferably monocyclic to tetracyclic radicals, most preferably monocyclic or bicyclic radicals such as phenyl, diphenyl, naphthyl, anthryl, phenanthryl and the like. Heterocyclic aromatic radicals $R_1$ and $R_2$ are preferably monocyclic to tricyclic radicals. These radicals may be entirely heterocyclic or may contain a heterocyclic ring and one or more fused benzene rings, and the cyano group can be linked both to the heterocyclic and to the isocyclic moiety respectively. Examples of heterocyclic aromatic radicals are pyridyl, pyrimidyl, pyrazinyl, triazinyl, furyl, pyrrolyl, thiophenyl, quinolyl, cumarinyl, benzfuranyl, benzimidazolyi, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, ortho-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridonyl, quinazolindionyl, quinoxalindionyl, benzoxazindionyl, benzoxazinonyl and naphthalimidyl. Both the isocyclic and the heterocyclic aromatic radicals may contain the customary non-watersolubilising substituents such as those described in U.S. Pat. No. 6,057,449.

Pyrrolo[3,4-c]pyrroles of the formula I, in which $R^1$ and $R^2$ independently of one another are a group of the formula

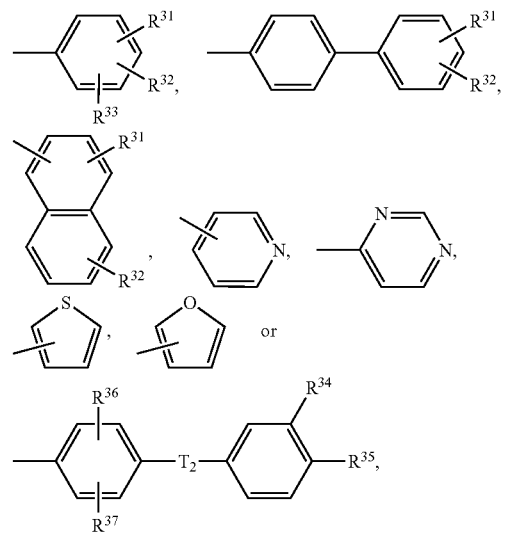

in which
$R^{31}$, $R^{32}$ and $R^{33}$ independently of one another are hydrogen, carbamoyl, $C_{2-18}$-alkylcarbamoyl, $C_{2-18}$-alkoxycarbonyl, $C_{2-18}$-alkanoylamino, halogen, $C_1$-$C_{24}$ alkyl, $C_1$-$C_6$ alkoxy, $C_1$-$C_{18}$alkylthio, $C_1$-$C_{18}$alkylamino, di($C_1$-$C_{18}$ alkyl)amino, —CN, —NO$_2$, phenyl, trifluoromethyl, $C_5$-$C_6$ cycloalkyl, —C=N—($C_1$-$C_{24}$ alkyl),

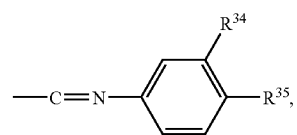

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, $T_2$ is —C(O)—NH—, —C(O)—O—, —NH—C(O)—, in particular —CH$_2$—, —CH(CH$_3$)—, —C(CH$_3$)$_2$—, —CH=N—, —N=N—, —O—, —S—, —SO—, —SO$_2$— or —NR$^{38}$—, R$^{34}$ and R$^{35}$ independently of one another are hydrogen, halogen, C$_{1-6}$-alkyl, C$_{1-6}$-alkoxy or —CN, R$^{36}$ and R$^{37}$ independently of one another are hydrogen, halogen or C$_{1-6}$-alkyl and R$^{38}$ is hydrogen or C$_1$-C$_6$-alkyl; are preferred and DPPs of the formula I, in which R$^1$ and R$^2$ are independently of each other a group of the formula

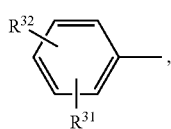

(Ib)

in which R$^{31}$ and R$^{32}$ independently of one another are hydrogen, methyl, tert-butyl, chlorine, bromine, CN or phenyl are especially preferred.

The preferred starting material employed in the preparation of compounds of the formula (I) according to this invention is a homogeneous nitrile of the formula (II) or (III). It is also preferred to use nitriles of the formula (II) and/or (III), wherein R$_1$ and R$_2$ are, each independently of the other, phenyl or said phenyl substituted by one or two chlorine atoms, by one or two methyl groups, by methoxy, by trifluoromethyl, by cyano, by methoxycarbonyl, by methyl, by tert-butyl, by dimethylamino or by cyanophenyl; naphthyl, biphenylyl; pyridyl or said pyridyl substituted by amyloxy; furyl or thienyl.

In particular, the starting materials employed are nitriles of the formula

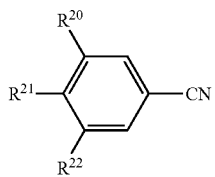

(Ia)

wherein each of R$^{20}$, R$^{21}$ and R$^{22}$, independently of one another, is hydrogen, fluorine, chlorine, bromine, carbamoyl, cyano, trifluoromethyl, C$_{2-10}$-alkylcarbamoyl, C$_{1-10}$-alkyl, C$_{1-10}$-alkoxy, C$_{1-10}$-alkylmercapto, C$_{2-10}$-alkoxycarbonyl, C$_{2-10}$-alkanoylamino, C$_{1-10}$-monoalkylamino, C$_{1-18}$-dialkylamino, phenyl or phenoxy, phenylmercapto, phenoxycarbonyl, phenylcarbamoyl or benzoylamino, each unsubstituted or substituted by halogen, C$_{1-4}$-alkyl or C$_{1-4}$-alkoxy, with the proviso that at least one of R$^{20}$, R$^{21}$ or R$^{22}$ is hydrogen.

Preferably, the starting materials employed are nitriles of the formula Ia, wherein R$^{20}$ is hydrogen and both R$^{21}$ and R$^{22}$ are hydrogen, or one of R$^{21}$ or R$^{22}$ is chlorine, bromine, C$_{1-4}$-alkyl, cyano, C$_{1-4}$-alkoxy, or is phenyl, phenoxy, carbamoyl or C$_{1-4}$-alkylcarbamoyl, each unsubstituted or substituted by chlorine or methyl, or is phenylcarbamoyl which is unsubstituted or substituted by chlorine, methyl or methoxy, and the other is hydrogen.

In a further preferred embodiment of the present process only one nitrile of formula (II) or of formula (III) is used.

A preferred embodiment of the present invention concerns a process wherein R$^1$ and R$^2$, each independently of the other, are phenyl or said phenyl substituted by one or two chlorine atoms, by one or two methyl groups, by methoxy, by trifluoromethyl, by cyano, by methoxycarbonyl, by methyl, by tert-butyl, by dimethylamino or by cyanophenyl; naphthyl, biphenylyl; pyridyl or said pyridyl substituted by amyloxy; furyl or thienyl, such as phenyl, 3-chlorophenyl, 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-methylphenyl, 4-tert-butylphenyl, 4-dimethylaminophenyl, 4-(para-cyanophenyl)phenyl, 1-naphthyl, 2-naphthyl, 4-biphenylyl, 2-pyridyl, 6-amyloxy-3-pyridyl, 2-furyl or 2-thienyl.

A particularly preferred embodiment of the present invention concerns a process wherein R$^1$ and R$^2$ each independently of the other, are phenyl, 3- or 4-chlorophenyl, 3- or 4-methylphenyl, 4-tert-butylphenyl, 4-biphenylyl, 3- or 4-cyanophenyl.

The disuccinates to be used in the process according to the invention include dialkyl, diaryl or monoalkyl-monoaryl succinates. The dialkyl and diaryl succinates may also be asymmetrical. However, it is preferred to use symmetrical disuccinates, most preferably symmetrical dialkyl succinates, most preferably symmetrical dialkyl succinates. If a diaryl or monoaryl-monoalkyl succinate is employed, aryl denotes preferably phenyl which is unsubstituted or substituted by halogen such as chlorine, C$_{1-6}$-alkyl such as ethyl, methyl, isopropyl or tert-butyl, or C$_{1-6}$-alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and more preferably 1 to 5, carbon atoms. Branched alkyl is preferably sec- or tert-alkyl, for example, isopropyl, sec-butyl, tert-butyl, tert-amyl and cyclohexyl.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1-dimethylpentyl]succinate, di-[1-methylethylbutyl]succinate, di-[1,1-diethylpropyl]succinate, diphenyl succinate, di-[4-methylphenyl]succinate, di-[4-chlorophenyl]succinate, monoethyl-monophenyl succinate, and dicyclohexyl succinate. Most preferably, the starting disuccinate is diisopropyl succinate.

The disuccinates and the nitriles of formula (II) or (III) are known compounds and may be prepared by known methods.

Typically, the nitrile and the disuccinate are used in stoichiometric proportions. It can be advantageous to use the nitrile to be reacted with the disuccinate in more than only stoichiometric proportions. It has been found that the yield of final product may be improved by using an excess of nitrile over disuccinate, in which case the optimum amount must be determined according to the respective reactants and may be up to ten times the stoichiometric amount required with respect to the disuccinate. It is normally possible to recover excess nitrile. An excess of disuccinate over the nitrile can often have a positive influence on the yield, in which case the excess may be up to twice the stoichiometrically required amount of disuccinate.

The reaction of the disuccinate with the nitrile is carried out in an organic solvent. Examples of suitable solvents are primary, secondary or tertiary alcohols containing 1 to 10 carbon atoms, for example, methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, for example, toluene, xylene, anisole or chlorobenzene; or aromatic heterocyclic compounds such as pyridine, picoline or quinoline. In addition, it is also possible to use the nitrile of formula (II) or (III) simultaneously as solvent if it is liquid in the temperature range in which the reaction takes place. Mixtures of the above solvents may also be used. It is convenient to use 5 to 20 parts be weight of solvent per 1 part by weight of reactants.

In the process according to the invention, it is preferred to use an alcohol as solvent, in particular a secondary or tertiary alcohol. Preferred tertiary alcohols are tert-butanol and tert-amyl alcohol. Mixtures of these preferred solvents with aromatic hydrocarbons such as toluene or xylene, or halogen-substituted benzene such as chlorobenzene, are also useful.

The process according to the invention is carried out in the presence of a strong base. Suitable strong bases are in particular the alkali metals themselves such as lithium, sodium or potassium, or alkali metal amides such as lithium amide, sodium amide or potassium amide, or alkali metal hydrides such as lithium, sodium or potassium hydride, or alkaline earth metal alcoholates or alkali metal alcoholates which are derived preferably from primary, secondary or tertiary aliphatic alcohols containing from 1 to 10 carbon atoms, for example, lithium methylate, sodium methylate or potassium methylate, or lithium, sodium or potassium ethylate, lithium, sodium or potassium n-propylate, lithium, sodium or potassium iso-propylate, lithium, sodium or potassium n-butylate, lithium, sodium or potassium sec-butylate, lithium, sodium or potassium tert-butylate, lithium, sodium or potassium 2-methyl-2-butylate, lithium, sodium or potassium 2-methyl-2-pentylate, lithium, sodium or potassium 3-methyl-3-pentylate, lithium, sodium or potassium 3-ethyl-3-pentylate or lithium, sodium or potassium 3-ethyl-3-pentylate. Additionally, a mixture of these bases may also be employed.

The preferred strong base is an alkali metal alcoholate, the alkali metals being preferably sodium or potassium and the alcoholate being preferably derived from a secondary or tertiary alcohol. Particularly preferred strong bases are therefore, for example, sodium or potassium isopropylate, sodium or potassium sec-butylate, sodium or potassium tert-butylate and sodium or potassium tert-amylate. Moreover, the alkali metal alcoholates may be prepared in situ by reacting the appropriate alcohol with the alkali metal, alkali metal hydride or alkali metal amide.

The strong base is employed in an amount of preferably from about 0.1 to about 10 moles, most preferably from about 1.9 to about 4.0 moles, based on one mole of the disuccinate. Although a stoichiometric amount of base may suffice, an excess of base has been found to have an advantageous effect on the yield.

Regulation in particle size of the 1,4-diketopyrrolo[3,4-c] pyrroles of formula (I) relative to the particle size of the unregulated form thereof becomes noticeable with the inclusion of as little as 0.1% of the particle growth regulator relative to the weight of the DPP compound of the formula I. The level of the regulator can be as high as 10% by weight. Although the particle growth regulator can be present in amounts greater than 10%, using more than said amount may adversely affect the color.

A variety of pigments having varying degrees of particle size and transparency require a range of from greater than 0.1%, for example 0.2%, to about 10% of the particle growth regulator. A preferred range of regulator incorporated during the reaction of the nitrile with the disuccinate to produce the pigmentary 1,4-diketopyrrolo[3,4-c]pyrrole of formula (I) and/or the conditioning step is the minimum amount necessary to directly prepare a pigmentary 1,4-diketopyrrolo[3,4-c]pyrrole up to about 10% by weight of the particle growth regulator, for example from 0.1% up to about 10% by weight. The preferred range of particle growth regulator is from 0.5 to 4% by weight, the most preferred range is from 0.5% to 2% by weight.

The surface area of the 1,4-diketopyrrolo[3,4-c]pyrrole product is directly related to the amount of the particle growth regulator present during the reaction and is inversely proportional to the particle size. Thus, the surface area of the product will increase as the amount of the particle growth regulator increases. In order for the 1,4-diketopyrrolo[3,4-c]pyrroles of formula (I) to be suitable for direct use as a pigment, the surface area of the reaction product should be at least 15 $m^2$/gram, for example in the range of from about 15 to about 50 $m^2$/gram, preferably from about 20 to 50 $m^2$/gram. The surface area can be measured by nitrogen absorption or another suitable method.

A preferred embodiment is to charge the reaction vessel with the nitrile and the base and then adding the disuccinate in the range of the reaction temperature, which addition order has a particularly advantageous effect on the yield. It is also possible to add the disuccinate and the nitrile simultaneously to the base. The process according to the invention may be carried out not only in a batchwise manner, but also continuously.

In particular, when using disuccinates containing alkyl radicals and alcoholates which are derived from lower alcohols such as methanol, ethanol, n-propanol, isopropanol or tert-butanol, it may be necessary to remove the lower alcohol formed during the reaction from the reaction medium continuously in order to obtain higher yields.

If an alcohol is used as solvent and an alcoholate as base, it may prove advantageous to choose an alcohol and alcoholate having the same alkyl moieties. It may likewise be advantageous if, in addition, the disuccinate also contains such alkyl groups.

The term "regulating the crystal growth" refers to controlling the synthesis of pigment particles to have a suitable pigmentary size and/or a narrow particle size distribution as well as directing the growth of the crystals to generate particles of a specifically desired shape, such as platelet, needle, cubic, leaflet, prismatic and other geometric forms and/or of a specifically desired rheology. Consequently, the better control of the crystal growth allows gaining samples with a narrower particle size distribution and/or a better crystal shape, or both together. The effect can be influenced by the chemical structure of the organic pigment, the selection of the reaction media and the concentration and chemical structure of the inventive particle growth regulator.

The conditioning step a) is carried out in water containing 0.0-100.0%, preferably 20.0-50.0% of a water-miscible solvent, at a conditioning temperature of 1° C. to the reflux temperature, preferably close to reflux temperature, optionally in the presence of an inorganic acid.

In general water-miscible solvents are selected from water-miscible alcohols, polyols, nitriles, organic acids, amides, esters, ethers, ketones, amines or a mixture of these solvents. Especially suitable water-miscible solvents include alcohols, in particular $C_{1-4}$-alkyl alcohols, such as methanol, ethanol, n- and isopranol, polyols, like glycols, such as ethylene glycol, diethylene glycol, ethers, like glycol ethers, such as ethylene glycol methyl ether, ethylene glycol ethyl ether, diethylene glycol monomethyl ether or diethylene glycol monoethylether, tetrahydrofuran (THF) and dioxane, organic acids, like acetic acid, ketones, like acetone, amines, such as mono-, di- or trialkylamines, such as propylamine, isopropylamine, diethylamine, dipropylamine, diisopropylamine, triethylamine, tripropylamine, triisopropylamine, bis(1-methyl)propylamine, 1,1-dimethylethylamine and 2-ethylhexylamine, aromatic amines, such as aniline, toluidine or phenylene diamine, and mixtures thereof.

Suitable inorganic acids are hydrochloric, sulphuric and phosphoric acid.

The conditioning step b) is carried out in an aprotic, water-miscible solvent in the presence of 0.0-99.0% water or in nonmiscible solvents with high boiling point or mixtures thereof at a conditioning temperature from 1° C. to the boiling point, most preferably 10-20° C. below the boiling point of the solvent.

Suitable aprotic, water-miscible solvents include acetonitrile, N-methyl-2-pyrrolidone (NMP), gamma-butyrolactone, dimethylsulfoxide (DMSO), N,N-dimethylacetamide (DMA), N,N-dimethylformamide (DMF), and mixtures thereof. Nonmiscible solvents include diphenylether, such as Dowtherm® E, nonmiscible alcohols, such as pentanol, hexanol and heptanol, nonmiscible aromatic solvents like toluene, xylene, o-dichlorobenzene, nonmiscible ketones, nonmiscible ethers and cyclic ethers, nonmiscible amines and aromatic amines, nonmiscible amides and esters and mixtures thereof.

The particle growth regulator of formula V or VI can be added in the heating step (a), the conditioning step (b) or the conditioning step (c).

The process of the present invention is illustrated below in further detail on the basis of preferred embodiments:

Process A-1:

The synthesis of the DPPs of the formula I is done in the presence of 0.1-20.0%, preferably 0.5-5.0% benzonitrile derivative of the formula IV, wherein the benzonitrile derivative is added at the beginning of the synthesis. That is, the nitrile of formula IV is, for example, charged to the reaction vessel with the nitriles of formula II and III and the base and then the disuccinate is added or the nitrile of formula IV is simultaneously added with the disuccinate and the nitrile to the base.

The conditioning is carried out in water containing 0.0-100.0%, preferably 20.0-50.0% of a water-miscible solvent, at a conditioning temperature of 1° C. to the reflux temperature, preferably close to reflux temperature.

Process A-2:

The synthesis of the DPPs of the formula I is done in the presence of 0.1-20.0%, preferably 0.25-2.0% DPP derivative of the formula V or VI, wherein the DPP derivative is preferably added at the beginning or at the end of the DPP synthesis, just before the conditioning. The conditioning is carried out in water containing 0.0-100.0%, preferably 20.0-50.0% of a water-miscible solvent, at a conditioning temperature of 1° C. to the reflux temperature, preferably close to reflux temperature.

Process B-1:

The synthesis of the DPPs of the formula I is done in the presence of 0.1-20.0%, preferably 0.5-5.0% nitrile of the formula IV, wherein the nitrile is preferably added at the beginning of the synthesis.

The first conditioning is carried out in water containing 0.0-100.0%, preferably 20.0-50.0% of a water-miscible solvent at a conditioning temperature of 1° C. to the reflux temperature, preferably 0-40° C., optionally in the presence of 1.0-99.0%, preferably 5.0-20.0% inorganic acid.

Suitable inorganic acids include hydrochloric, phosphoric and in particular sulphuric acid.

The second conditioning is carried out in an aprotic, water-miscible solvent in the presence of 0.0-99.0% water at a conditioning temperature from 1° C. to the boiling point, most preferably 10-20° C. below the boiling point of the solvent or in a non-miscible solvent with a high boiling point at a conditioning temperature from room temperature to the boiling point, preferably 10-20° C. below the boiling point of the solvent.

Process B-2:

The synthesis of the DPPs of the formula I is done in the presence of 0.1-20.0%, preferably 0.25-2.0% DPP derivatives of formula V or VI, wherein the DPP derivatives of formula V or VI are added at the beginning or at the end of the DPP synthesis, just before the first conditioning.

The first conditioning is carried out in water containing 0.0-100.0%, preferably 20.0-50.0% of a water-miscible solvent at a conditioning temperature of 1° C. to the reflux temperature, preferably 0-40° C., optionally in the presence of 1.0-99.0%, preferably 5.0-20.0% inorganic acid.

The second conditioning is carried out in an aprotic, water-miscible solvent in the presence of 0.0-99.0% water at a conditioning temperature from 1° C. to the boiling point, most preferably 10-20° C. below the boiling point of the solvent or in a non-miscible solvent with a high boiling point at a conditioning temperature from room temperature to the boiling point, preferably 10-20° C. below the boiling point of the solvent.

Process C:

The synthesis of the DPPs of formula I is done without the addition of a crystal growth director of formula IVa, IVb, IVc, V or VI.

The first conditioning is carried out in water containing 0.0-100.0%, preferably 20.0-50.0% of a water-miscible solvent at a conditioning temperature of 1° C. to the reflux temperature, preferably 1°-40° C., optionally in the presence of 1.0-99.0%, preferably 5.0-20.0% inorganic acid.

The second conditioning is carried out in an aprotic, water-miscible solvent in the presence of 0.0-99.0% water at a conditioning temperature from 1° C. to the boiling point, most preferably 10-20° C. below the boiling point of the solvent or in a non-miscible solvent with a high boiling point at a conditioning temperature from room temperature to the boiling point, preferably 10-20° C. below the boiling point of the solvent in the presence of 0.1-20.0%, preferably 0.25-2.0% of the DPP derivatives of formula V or VI.

The nitrile compound of formula

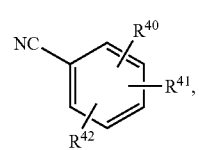

(IV)

wherein $R^{40}$, $R^{41}$ and $R^{42}$ are independently of each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$ or $SO_2R^9$; wherein $R^5$ and $R^6$ are hydrogen, linear or branched $C_{1-10}$-alkyl, $C_{5-10}$-cycloalkyl or $C_{6-10}$-aryl, $R^7$ is hydrogen, linear or branched $C_{1-10}$-alkyl, $C_{5-10}$-cycloalkyl or $C_{6-10}$-aryl, $R^9$ is hydrogen, linear or branched $C_{1-10}$-alkyl, $C_{5-10}$-cycloalkyl, $C_{7-10}$-aralkyl, $C_{6-10}$-aryl or $NR^{10}R^{11}$, wherein $R^{10}$ and $R^{11}$ are hydrogen, linear or branched $C_{1-10}$-alkyl, $C_{7-10}$-aralkyl or $C_{6-10}$-aryl; is added in Process A-1 and B-1 at the beginning of the synthesis, wherein particle growth regulators of the formula

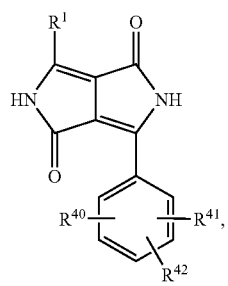

(IVa)

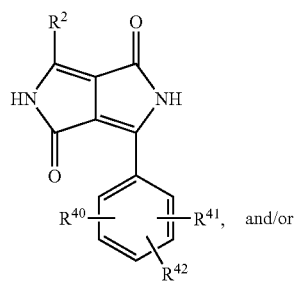

(IVb) and/or

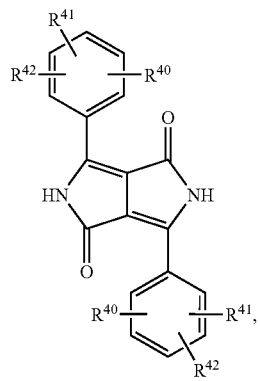

(IVc)

are obtained, wherein $R^1$, $R^2$, $R^{40}$, $R^{41}$ and $R^{42}$ are as defined above. It is preferred that the nitrile of formula IV is charged to the reaction vessel with the nitriles of formula II and III and the base and then the disuccinate is added or the nitrile of formula IV is simultaneously added with the disuccinate and the nitriles of formula II and III to the base, wherein the formation of the crystal growth regulators of the formula IVa and IVb is favored. In addition it is preferred that the nitriles of the formula II and III are identical, so that only one crystal growth regulator of formula IVa or IVb is formed.

Most preferred are compounds of formula

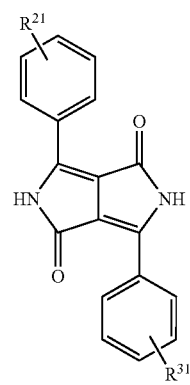

(IVa)

wherein $R^{31}$ is o-, m- or p-$C_{1-10}$-alkoxy, in particular o-, m- or p-$C_{1-4}$alkoxy, cyano, in particular m-CN, o- or m-chloro and $R^{21}$ is hydrogen, p-phenyl, $C_{1-10}$-alkyl, in particular m- or p-methyl and p-tert-butyl, p- or m-chloro, cyano, in particular m-cyano.

The DPP derivatives of the formula V

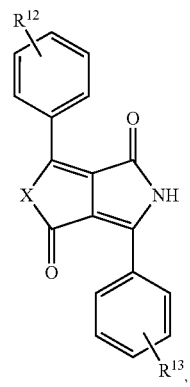

(V)

wherein X is O, S or $NR^{14}$, wherein $R^{14}$ is linear or branched $C_{1-10}$-alkyl, $C_{7-10}$-aralkyl or $C_{6-10}$-aryl; $R^{12}$ and $R^{13}$ are independently from each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$ or $SO_2R^9$; wherein $R^5$ and $R^6$ are hydrogen, linear or branched $C_{1-10}$-alkyl, $C_{5-10}$-cycloalkyl or $C_{6-10}$-aryl, $R^7$ is hydrogen, linear or branched $C_{1-10}$-alkyl, $C_{5-10}$-cycloalkyl or $C_{6-10}$-aryl, $R^9$ is hydrogen, linear or branched $C_{1-10}$-alkyl, $C_{5-10}$-cycloalkyl, $C_{7-10}$-aralkyl, $C_{6-10}$-aryl or $NR^{10}R^{11}$, wherein $R^{10}$ and $R^{11}$ are hydrogen, linear or branched $C_{1-10}$-alkyl, $C_{7-10}$-aralkyl or $C_{6-10}$-aryl; are especially preferred as crystal growth directors in Process A-2, B-2 and C. Most preferred are compounds of the formula V, wherein X is O or $NR^{14}$, wherein $R^{14}$ is $C_{1-4}$-alkyl or benzyl; $R^{12}$ and $R^{13}$ independently from each other hydrogen, $C_{1-4}$-alkyl, $C_{1-4}$-alkoxy or $C_{1-4}$-thioalkyl, halogen, CN or $SO_2R^9$, wherein $R^9$ is $C_{1-4}$-alkyl, phenyl, benzyl or $NR^{10}R^{11}$, wherein $R^{10}$ and $R^{11}$ are hydrogen, $C_{1-4}$-alkyl, benzyl or phenyl. Compounds, wherein $R^{12}$ and $R^{13}$ are identical are particularly preferred. Compounds of formula V, wherein X is O or S, except 3,5,6-triphenyl-1H-furo[3,4-c]pyrrole-1,4-(5H)-dione (U.S. Pat. No. 5,354,869), are novel and represent a further embodiment of the present invention.

The DPPs of the formula

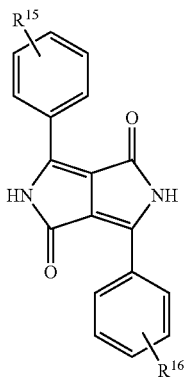

wherein $R^{15}$ and $R^{16}$ are independently from each other hydrogen, linear or branched $C_{1-10}$-alkyl, $C_{1-10}$-alkoxy or $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, CN, $CONR^5R^6$, $C(O)OR^7$, $SO_2R^{10}$, wherein
$R^5$ and $R^6$ are hydrogen, linear or branched $C_{1-10}$-alkyl, $C_{5-10}$-cycloalkyl or $C_{6-10}$-aryl,
$R^7$ is hydrogen, linear or branched $C_{1-10}$-alkyl, $C_{5-10}$-cycloalkyl or $C_{6-10}$-aryl,
$R^9$ is hydrogen, linear or branched $C_{1-10}$-alkyl, $C_{5-10}$-cycloalkyl, $C_{6-10}$-aryl or $NR^{10}R^{11}$, wherein $R^{10}$ and $R^{11}$ are hydrogen, linear or branched $C_{1-10}$-alkyl or $C_{6-10}$-aryl, wherein $R^{15}$ and $R^{16}$ are preferably different from each other, are especially preferred as crystal growth regulators in Process A-2, B-2 and C. DPPs of the formula VI, wherein $R^{15}$ is hydrogen, 4-phenyl, 3- or 4-chloro, 3- or 4-methyl, 4-tert-butyl, 3- or 4-cyano and wherein $R^{16}$ is o-, m- or p-$C_{1-10}$-alkoxy, in particular o-, m- or p-$C_{1-4}$-alkoxy, cyano, in particular m-CN, o- or m-chloro are particularly preferred, wherein $R^{15}$ and $R^{16}$ are different from each other.

The present invention provides a process for a very opaque and saturated form of C.I. Pigment Red 254, a very opaque, heat stable form of C.I. Pigment Red 255 as well as a very strong and saturated form of C.I. Pigment Red 272.

The compounds of formula (I) are used as colorants for high molecular weight organic materials and can be used directly in the form in which they are obtained.

Depending on the end use, it may be advantageous to prepare mixtures of compounds of the formula (I). This can be done for example by mixing different reaction mixtures which have been prepared independently of one another before the protolysis, protolyzing them together and then isolating the resultant mixture of compounds of the formula (I). It is also possible to precipitate two or more compounds of the formula (I) together.

The present invention relates to pigment compositions comprising
a) a 1,4-diketopyrrolo[3,4-c]pyrrole of the formula (I); and
b) an effective crystal growth directing amount of a compound of formula IVa, IVb and/or IVc or V or VI.

The particle growth regulator is present in an amount of between 0.1 and 10 weight %, based on the weight of the diketopyrrolopyrrole. A more useful range of particle growth regulator is from 0.5% to 4%, in particular 0.5% to 2% by weight of the particle growth regulator.

Organic materials of high molecular weight which may be pigmented with the inventive pigment compositions comprising compounds of formula (I) are for example cellulose ethers and esters such as ethyl cellulose, nitrocellulose, cellulose acetate or cellulose butylate, natural resins or synthetic resins such as polymerization resins or condensation resins, for example, aminoplasts, in particular urea/formaldehyde and melamine/formaldehyde resins, alkyd resins, phenolic plastics, polycarbonates, polyolefins such as polystyrene, polyvinyl chloride, polyethylene, polypropylene, polyacrylonitrile, polyacrylates polyamides, polyurethanes or polyesters, rubber, casein, silicone and silicone resins, individually or in mixtures.

It is immaterial whether the above organic compounds of high molecular weight are in the form of plastics, melts or of spinning solutions, lacquers, paints or painting inks. Depending on the end use, it is advantageous to use the pigments of this invention in the form of toners or formulations. The high molecular weight organic compounds mentioned can be present individually or in mixtures. The inventive pigment compositions comprising compounds of the formula (I) are employed in an amount of about 0.01 to about 30%, preferably from about 0.1 to about 10%, by weight, based on the organic material of high molecular weight to be pigmented.

The colorations obtained, for example in plastics, filaments, lacquers or printing inks, have excellent tinctorial strength, good dispersibility, good fastness to overspraying, migration, heat, light and atmospheric influences, as well as good gloss.

The high molecular weight organic substances are pigmented with the inventive pigment compositions comprising pigments of formula (I), for example, by mixing such a pigment, if desired, in the form of a masterbatch, into these substrates using roll mills and mixing or grinding apparatus. The pigmented material is then brought into the desired final form by known methods, such as calendaring, pressing, extruding, brushing, casting or injection molding. It may be desirable to incorporate plasticizers into the high molecular weight compounds before starting operation in order to produce non-rigid moldings or to reduce their brittleness. Suitable plasticizers are, for example, esters of phosphoric acid, phthalic acid or sebacic acid. Plasticizers can be incorporated before or after the incorporation of pigments according to the invention. To obtain different shades, it is further possible to add fillers or other coloring constituents, such as white, colored, or black pigments, in any desired amounts, to the high molecular weight organic substances, in addition to the pigments according to the invention.

The pigments prepared by the present process are particularly suitable for coloring polyvinyl chloride and polyolefins, such as polyethylene and polypropylene, Engineering PoLymers, like poly(methyl methacrylate), polycarbonate, polystyrene, ABS, PET, polyamide etc., and for pigmenting lacquers and paints in particular for full shade automotive topcoats. When used for this purpose, the pigments prepared in accordance with the present invention possess good general pigment properties such as high dispersability, high saturation and purity and high migration, heat, light and weathering fastness properties.

The following examples are for purposes of illustration, and are not intended to limit the scope of the present invention in any manner whatsoever. Parts and percentages are by weight unless otherwise specified.

EXAMPLES

Comparison Example 1

EP-A-640 603

In a 200 ml four-necked round-bottomed flask equipped with a glass stirrer, a thermometer, a nitrogen inlet tube, a bubble counter and an addition funnel, 60.0 g t-amylalcohol and 5.24 g solid sodium are poured. The mixture is heated to 130° C. (external temperature) and a small amount of iron(III) trichloride is added. After the solid sodium has completely disappeared, a mixture of 15.21 g 4-chlorobenzonitrile, 14.27 g diisopropylsuccinimide and 42.70 g t-amylalcohol is added within 2 h. The temperature is decreased to 85° C. (internal temperature) and the reaction mixture is stirred for 2 h. The temperature is decreased to 40° C. and the reaction mixture is transferred within 15 minutes to a next reactor containing a mixture of 300 ml demineralised water and 300 ml methanol at 40° C. The temperature is set to reflux (78° C.) and the pigment is conditioned during 18 h. After filtration and drying in an oven under vacuum 16.03 g (83%) bright red pigment are obtained (C. I. Pigment Red 254 of Comparative Example (CC-1).

Example 1

In a 1500 ml four-necked round-bottomed reactor equipped with a glass stirrer, a thermometer, a nitrogen inlet tube, a bubble counter, an addition funnel and a reflux condenser, 800 ml toluene, 14.1 g sodium hydroxide previously dissolved in 350 ml demineralised water, 3.5 g tetraethylammoniumbromide and 40.0 g 4-hydroxybenzonitrile were poured. Under vigorous stirring, 82.7 g 2-bromopropane are added within 5 minutes. The emulsion is heated at reflux during 18 hrs. The organic phase is separated, and extracted with 300 ml 1 mol/l NaOH solution and 300 ml saturated NaCl solution. The solvent is evaporated. The impure solid is recrystallised in 110 ml hexane. Yield: 28.3 g (52.3%) pure 4-isopropoxybenzonitrile.

In a 750 ml four-necked round-bottomed reactor equipped with a glass stirrer, a thermometer, a nitrogen inlet tube, a reflux condenser, a bubble counter and a double-walled addition funnel, 300.0 g t-amylalcohol and 10.29 g solid sodium are pored. The mixture is heated to 130° C. (ext. temperature) and a small amount of iron(III) trichloride is added. After the metallic sodium has completely disappeared, a mixture of 30.13 g 4-chlorobenzonitrile, 1.21 g 4-isopropoxybenzonitrile, 33.84 g diisopropylsuccinimide and 60.0 ml t-amylalcohol is added within 2 hours. The temperature is decreased to 85° C. (int.) and the reaction mixture is stirred further 2 hours. The temperature is decreased to 40° C. and the reaction mixture is transferred to a next reactor within 30 minutes and poured into a mixture of 500 ml demineralised water and 500 ml methanol at 40° C. The pigment is conditioned during 18 hours at reflux temperature (78° C.). After filtration and drying, 29.58 g (75%) of a red pigment powder are obtained.

25.0 g of the pigment powder are poured into 500 ml Dowtherm E and further conditioned 5 hours at 160° C. After filtration, washing and drying, 23.30 g (overall yield 70%) bright red pigment are obtained, that in comparison to the product of the Comparative Example, exhibits in mass tone a purer, brighter and yellower shade, along with a slightly higher opacity. In white reduction (5:95) the pigment shows considerably higher colour strength than CC-1 and the weather stability (2000 h WOM) is comparable to CC-1. The X-ray diffraction spectrum is similar to CC-1, but the slightly broader peak width indicates a lower average particle size. Joyce-Löbl measurements indicate a narrower particle size distribution than CC-1.

Example 2

In a 750 ml four-necked round-bottomed reactor equipped with a glass stirrer, a thermometer, a nitrogen inlet tube, a reflux condenser, a bubble counter and a double-walled addition funnel, 100.0 g t-amylalcohol and 3.43 g solid sodium are poured. The mixture is heated to 130° C. (ext. temperature) and a small amount of iron(III) trichloride is added. After the metallic sodium has completely disappeared, 11.24 g pyrrolinone of formula

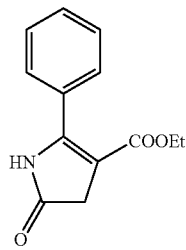 [SMILES: CCOC(=O)C1=C(c2ccccc2)NC(=O)C1]

are added (EP-A-0 511 165). The temperature is lowered to 90° C. and 7.32 g 2-methoxybenzonitrile dissolved in 25 ml t-amylalcohol are added within 3 hours. The reaction mixture is stirred further 1 hour, and poured into a beaker containing 250 ml methanol and 250 ml demineralised water. The suspension is filtered and the resulting solid is carefully washed with methanol and water. After drying 5.36 g (31.3%) red-orange 3-(2-methoxyphenyl)-6-phenylpyrrolo[3,4-c]pyrrole are obtained.

In a 250 ml four-necked round-bottomed reactor equipped with a glass stirrer, a thermometer, a nitrogen inlet tube, a reflux condenser, a bubble counter and a double-walled addition funnel, 60.0 g t-amylalcohol and 5.24 g solid sodium are poured. The mixture is heated to 130° C. (ext. temperature) and a small amount of iron(III) trichloride is added. After the metallic sodium has completely disappeared, 0.356 g 3-(2-methoxyphenyl)-6-phenylpyrrolo[3,4-c]pyrrole and a mixture of 14.19 g 4-chlorobenzonitrile, 10.72 g diisopropylsuccinimide and 32.7 g t-amylalcohol are added within 2 hours. The temperature is decreased to 85° C. (int.) and the reaction mixture is stirred further for 2 hrs. The temperature is decreased to 40° C. and the reaction mixture is transferred to a next reactor containing a mixture of 300 ml demineralised water, 300 ml methanol and 120 ml sulphuric acid at 40° C. within 15 minutes. The pigment is conditioned during 18 hrs at 40° C. After filtration and drying, 13.01 g (67%) dark red pigment powder are obtained.

The pigment powder is poured into 300 ml dimethylacetamide and further conditioned 5 hrs at 140° C. After filtration, washing and drying 11.53 g (overall yield 60%) bright red pigment are obtained, that in comparison to the Comparative Example exhibits in mass tone a purer, brighter and yellower shade, along with a higher opacity. In white reduction (5:95), the pigment shows slightly higher colour strength than CC-1 and the weather stability (2000 h WOM) is comparable to CC-1. The X-ray diffraction spectrum is similar to CC-1, but Joyce-Löbl measurements indicate a narrower particle size distribution than CC-1.

Example 3

In a 250 ml four-necked round-bottomed reactor equipped with a glass stirrer, a thermometer, a nitrogen inlet tube, a reflux condenser, a bubble counter and a double-walled addition funnel 60.0 g t-amylalcohol and 5.24 g solid sodium are poured. The mixture is heated to 130° C. (ext. temperature) and a small amount of iron(III) trichloride is added. After the metallic sodium has completely disappeared, a mixture of 14.63 g 4-chlorobenzonitrile, 10.72 g diisopropylsuccinimide and 32.7 g t-amylalcohol is added within 2 hours. The temperature is decreased to 85° C. (int.) and the reaction mixture is stirred further for 2 hours. The temperature is decreased to 40° C. and the reaction mixture is transferred within 15 minutes to a next reactor containing a mixture of 300 ml demineralised water, 300 ml methanol and 120 ml sulphuric acid at 40° C. The pigment is conditioned during 18 hours at 40° C. After filtration and drying 16.5 g (85%) dark red pigment powder are obtained.

In a four-necked round-bottomed reactor equipped with a glass stirrer, a thermometer, a nitrogen inlet tube, a reflux condenser, a bubble counter and a double-mantel addition funnel, 100.0 g t-amylalcohol and 3.43 g solid sodium are poured. The mixture was heated to 130° C. (ext. temperature) and a small amount of iron(III) trichloride is added. After the metallic sodium has completely disappeared, 11.56 g pyrrolinone of formula

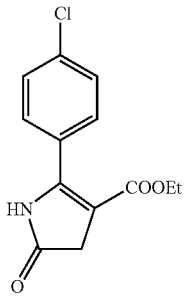

is added (EP-A-0511165). The temperature is lowered to 90° C., and 7.32 g 3-methoxy-benzonitrile dissolved in 25 ml t-amylalcohol are added within 3 hrs. The reaction mixture is stirred further for 1 hour and poured into a beaker containing 250 ml methanol and 250 ml demineralised water. The suspension is filtered and the resulting solid is carefully washed with methanol and water. After drying, 6.60 g (43.0%) red-orange 3-(4-chlorophenyl)-6-(3-methoxyphenyl)pyrrolo[3,4-c]pyrrole are obtained.

15.0 g pigment powder and 0.15 g 3-(4-chlorophenyl)-6-(3-methoxyphenyl)pyrrolo[3,4-c]pyrrole are poured into 300 ml dimethylacetamide and recrystallised 5 hours at 140° C. After filtration, washing and drying 14.7 g bright red pigment are obtained, that in comparison to the Comparative Example exhibits in mass tone a purer, brighter and yellower shade, along with a much higher opacity. In white reduction (5:95) the pigment shows higher colour strength than CC-1 and the weather stability (2000 h WOM) is comparable to CC-1. The X-ray diffraction spectrum is similar to CC-1, but the slightly broader peak width indicates a lower average particle size. Joyce-Löbl measurements indicate a narrower particle size distribution than CC-1.

Example 4

In a 250 ml four-necked round-bottomed reactor equipped with a glass stirrer, a thermometer, a nitrogen inlet tube, a reflux condenser, a bubble counter and a double-walled addition funnel 150.0 g t-amylalcohol and 5.15 g solid sodium are poured. The mixture is heated to 130° C. (ext. temperature) and a small amount of iron(III) trichloride is added. After the metallic sodium has completely disappeared, a mixture of 15.17 g 4-chlorobenzonitrile, 0.50 g 3-methoxybenzonitrile, 16.92 g diisopropylsuccinimide and 30.0 ml t-amylalcohol is added within 2 hours. The temperature is decreased to 85° C. (int.) and the reaction mixture is stirred further 2 hours. The temperature is decreased to 40° C. and the reaction mixture is transferred to a next reactor containing a mixture of 300 ml demineralised water, 300 ml methanol and 120 ml sulphuric acid at 40° C. within 30 minutes. The pigment is conditioned during 18 hrs at 40° C. After filtration and drying, 15.20 g (77%) of a red pigment powder are obtained. 15.0 g of the pigment powder are poured into 300 ml dimethylacetamide and further conditioned 5 hours at 140° C. After filtration, washing and drying 14.20 g (overall yield 72%) bright red pigment are obtained whose colour and fastness properties are very close to the pigment of Example 3.

Example 5

Example 3 is repeated, except that instead of 0.15 g 3-(4-chlorophenyl)-6-(3-methoxyphenyl)pyrrolo[3,4-c]pyrrole 0.15 g of the DPP derivative of formula

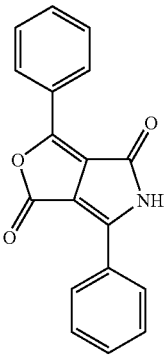

are used (EP Application No, 01810773.0 filed Aug. 10, 2001 priority document for WO 2003/014255). A bright red pigment is obtained which in comparison to the Comparative Example exhibits in mass tone a purer, brighter and yellower shade. its opacity is similar to CC-1, In white reduction (95:5), the pigment shows considerably higher colour strength. The X-ray diffraction spectrum is similar to CC-1, but the broader peak width indicates a lower average particle size.

Example 6

Example 3 is repeated, except that instead of 0.15 g 3-(4-chlorophenyl)-6-(3-methoxy-phenyl)pyrrolo[3,4-c]pyrrole 0.15 g of the DPP compound of formula

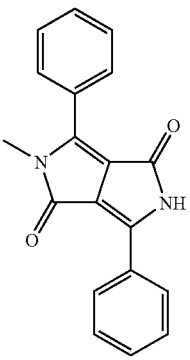 [SMILES: CN1C(=O)C2=C(c3ccccc3)NC(=O)C2=C1c1ccccc1]

(W09608537) are used. A bright red pigment is obtained which in comparison to the Comparative Examples exhibits in mass tone a purer, brighter and yellower shade. The opacity is similar to CC-1. In white reduction (95:5), the pigment shows considerably higher colour strength than CC-1 and the weather stability (2000 h WOM) is comparable to CC-1. The X-ray diffraction spectrum is similar to CC-1, but the broader peak width indicates a lower average particle size.

Example 7

Example 4 is repeated, except that 3-methoxybenzonitrile is replaced by 4-isopropoxybenzonitrile. A bright red pigment is obtained that in comparison to the Comparative Examples exhibits in mass tone a purer, brighter and yellower shade, along with a higher opacity. In white reduction (5:95) the pigment shows higher colour strength than CC-1 and the weather stability (2000 h WOM) is comparable to CC-1. The X-ray diffraction spectrum is similar to CC-1. Joyce-Löbl measurements indicate a narrower particle size distribution than CC-1.

Example 8

Example 7 is repeated, except that dimethylacetamide is replaced by dimethylformamide. We obtain a bright red pigment that in comparison to the Comparative Examples exhibits in mass tone a purer, brighter and yellower shade, along with a slightly higher opacity. In white reduction (5:95) the pigment shows considerably higher colour strength than CC-1 and the weather stability (2000 h WOM) is comparable to CC-1. The X-ray diffraction spectrum is similar to CC-1, but the broader peak width indicates a lower average particle size. Joyce-Löbl measurements indicate a clearly narrower particle size distribution than CC-1.

Example 9

Example 4 is repeated, but the conditioning is achieved in water/methanol 1:1 at reflux temperature (78° C.) during 18 hours. A red-orange pigment powder is obtained that in comparison to the Comparative Examples exhibits a considerably yellower shade. The opacity is slightly lower than CC-1. In white reduction (95:5) the colour strength is considerably stronger than CC-1. The X-ray diffraction spectrum is similar to CC-1, but the broader peak width indicates a lower average particle size.

Test Method 4.0 g untreated pigment are added to 46.0 g AM-paint prepared as described below. The paint at 8% pigment concentration is dispersed 1 hour in Skandex with 200 g glass beads (diameter 2 mm). The dispersed paint is drawn down (100 µm) on a Mylar sheet and poured out on a glass plate. After 10 minutes the Mylar sheet and the glass plate are allowed to dry 30 minutes at 130° C. in a hot air oven. The following colour properties of the Mylar sheet are measured using a Datacolor 3890 colorimeter: lightness L*, chroma C*, hue h and opacity (as ΔTr. over black). The contrast paper is a clean and new standard Leneta.

A white reduction containing 5 parts of pigment and 95 parts of white pigment are prepared as follows: 3.27 g of the previously prepared mass tone paint are added to 26.73 g white AM-paint (description below) and mixed with a simple glass stirrer to yield 30 g white reduction, which is drawn down on a Mylar sheet (100 µm). From the Mylar sheet the colour strength is assessed.

Preparation of the AM-Paint

Mass Tone:
   60.00 parts per weight Bayer Alkydal F 310 (60% in solvent naphtol)
   16.00 parts per weight Cytec Cymel 327 (90% in isobutanol)
   19.00 parts per weight xylol
   2.00 parts per weight butanol
   2.00 parts per weight 1-methoxy-2-propanol
   1.00 parts per weight silicone oil A (1% in xylol)

White Reduction:
   20.00 parts per weight titanium dioxide Kronos 2310
   47.67 parts per weight Bayer Alkydal F 310 (60% in solvent naphtol)
   12.75 parts per weight Cytec Cymel 327 (90% in butanol)
   0.50 parts per weight Aerosil 200
   1.59 parts per weight 1-methoxy-2-propanol
   1.59 parts per weight butanol
   15.10 parts per weight xylol
   0.80 parts per weight silicone oil A (1% in xylol)

The invention claimed is:
1. A pigment composition comprising:
a) a 1,4-diketopyrrolo[3,4-c]pyrrole of the formula (I)

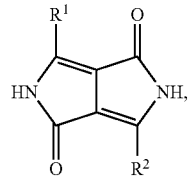

(I)

wherein
R$^1$ and R$^2$ independently of each other are

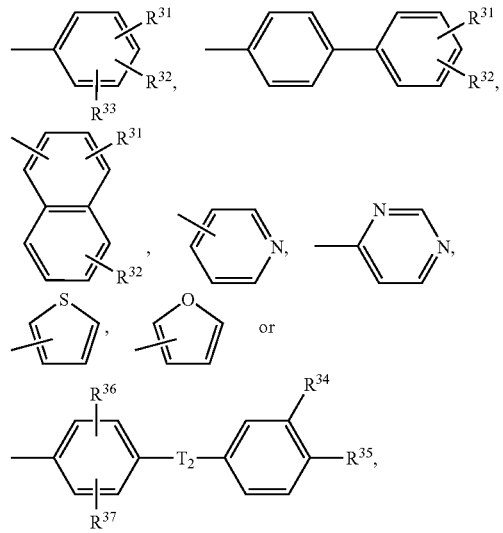

R$^{31}$, R$^{32}$, and R$^{33}$ independently of one another are hydrogen, carbamoyl, C$_{2-18}$-alkylcarbamoyl, C$_{2-18}$-alkoxycarborlyl, C$_{2-18}$-alkanoylamino, halogen, C$_1$-C$_{24}$alkyl, C$_1$-C$_6$alkoxy, C$_1$-C$_{18}$alkylthio, C$_1$-C$_{18}$alkylamino, di(C$_1$-C$_{18}$alkyl)amino, —CN, —NO$_2$, phenyl, trifluoromethyl, C$_5$-C$_6$cycloalkyl, —C=N—(C$_1$-C$_{24}$alkyl),

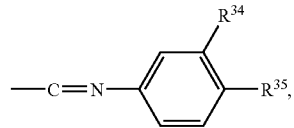

imidazolyl, pyrazolyl, triazolyl, piperazinyl, pyrrolyl, oxazolyl, benzoxazolyl, benzothiazolyl, benzimidazolyl, morpholinyl, piperidinyl, or pyrrolidinyl, T$_2$ is —C(O)—NH—, —C(O)—O—, —NH—C(O)—, —CH$_2$—, —CH(CH$_3$)—, —C(CH$_3$)$_2$—, —CH=N—, —N=N—, —O—, —S—, —SO—, —SO$_2$—, or —NR$^{38}$—, R$^{34}$ and R$^{35}$ independently of one another are hydrogen, halogen, C$_{1-6}$-alkyl, C$_{1-6}$-alkoxy, or —CN, R$^{36}$ and R$^{37}$ independently of one another are hydrogen, halogen, or C$_{1-6}$-alkyl, and $R^{38}$ is hydrogen or $C_1$-$C_6$-alkyl; and b) from 0.5 to 4 weight % based on the weight of the 1,4-diketopyrrolo[3,4-c]pyrrole of formula (I) of a compound of formula (V)

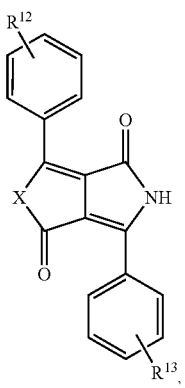

(V)

wherein

X is O, S, or $NR^{14}$, wherein $R^{14}$ is linear or branched $C_{1-10}$-alkyl, $C_{7-10}$-aralkyl, or $C_{6-10}$-aryl;

$R^{12}$ and $R^{13}$ are independently of each other hydrogen, linear or branched $C_{1-10}$-alkyl, linear or branched $C_{1-10}$-alkoxy, linear or branched $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, $CONR^5R^6$, $C(O)OR^7$, or $SO_2R^9$;

$R^5$ and $R^6$ are hydrogen, linear or branched $C_{1-10}$-alkyl, $C_{5-10}$-cycloalkyl, or $C_{6-10}$-aryl, $R^7$ is hydrogen, linear or branched $C_{1-10}$-alkyl, $C_{5-10}$-cycloalkyl, $C_{7-10}$-aralkyl, or $C_{6-10}$-aryl, and $R^9$ is hydrogen, linear or branched $C_{1-10}$-alkyl, $C_{5-10}$-cycloalkyl, $C_{7-10}$-aralkyl, $C_{6-10}$-aryl, or $NR^{10}R^{11}$, wherein $R^{10}$ and $R^{11}$ are hydrogen, linear or branched $C_{1-10}$-alkyl, $C_{7-10}$-aralkyl, or $C_{6-10}$-aryl.

2. A high molecular weight organic material pigmented with a pigment composition of claim 1.

3. A pigment composition according to claim 1, wherein the 1,4-diketopyrrolo[3,4-c]pyrrole of formula (I) is a compound of formula (I) in which $R^1$ and $R^2$ are independently of each other a group of formula (Ib)

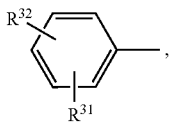

(Ib)

wherein $R^{31}$ and $R^{32}$ independently of one another are hydrogen, methyl, tert-butyl, chlorine, bromine, CN, or phenyl.

4. The pigment composition according to claim 1, wherein X is O or $NR^{14}$, wherein $R^{14}$ is $C_{1-4}$-alkyl or benzyl;

$R^{12}$ and $R^{13}$ are independently from each other hydrogen, $C_{1-4}$-alkyl, $C_{1-4}$-alkoxy, $C_{1-4}$-thioalkyl, halogen, or $SO_2R^9$, and $R^9$ is $C_{1-4}$-alkyl, phenyl, benzyl, or $NR^{10}R^{11}$, wherein $R^{10}$ and $R^{11}$ are hydrogen, $C_{1-4}$-alkyl, benzyl, or phenyl.

5. The pigment composition according to claim 1, wherein $R^{14}$ is selected from the group consisting of ethyl, n-propyl, isopropyl, n-butyl, sec-butyl, isobutyl, tert-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl, and octadecyl; and $R^{12}$ and $R^{13}$ are independently of each other hydrogen, linear or branched $C_{1-10}$-alkyl, linear or branched $C_{1-10}$-alkoxy, -linear or branched $C_{1-10}$-thioalkyl, $C_{5-10}$-cycloalkyl, $C_{6-10}$-aryloxy, $C_{6-10}$-arylthio, $C_{7-10}$-aralkyloxy, $C_{7-10}$-aralkylthio, halogen, $CONR^5R^6$, $C(O)OR^7$, or $SO_2R^9$.

6. A pigment composition comprising:

a) a 1,4-diketopyrrolo[3,4-c]pyrrole of the formula (I)

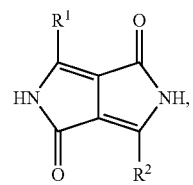

(I)

wherein $R^1$ and $R^2$ are independently of each other a group of formula (Ib)

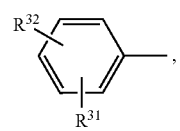

(Ib)

wherein $R^{31}$ and $R^{32}$ independently of one another are hydrogen, methyl, tert-butyl, chlorine, bromine, CN, or phenyl;

and b) from 0.5 to 4 weight % based on the weight of the 1,4-diketopyrrolo[3,4-c]pyrrole of formula (I) of a compound of formula (VI)

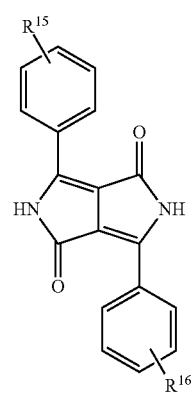

(VI)

wherein $R^{15}$ is hydrogen, 4-phenyl, 3- or 4-chloro, 3- or 4-methyl, or 4-tert-butyl; and $R^{16}$ is o-, m- or p-$C_{1-10}$-alkoxy, or o- or m-chloro, wherein $R^{15}$ and $R^{16}$ are different from each other, with the proviso that when $R^{16}$ is m-chloro, $R^{15}$ is not hydrogen;

and
wherein the 1,4-diketopyrrolo[3,4-c]pyrrole of formula (I) is different from the compound of formula (VI).

7. The pigment composition according to claim 6, wherein $R^{16}$ is o-, m- or p-$C_{1-10}$-alkoxy, or o-chloro.

8. The pigment composition according to claim 6, wherein $R^{15}$ is 3- or 4-chloro, and $R^{16}$ is o-chloro.

9. The pigment composition according to claim 6, wherein $R^{15}$ is 3- or 4-chloro, and $R^{16}$ is o-, m- or p-$C_{1-4}$-alkoxy.

10. A high molecular weight organic material pigmented with a pigment composition of claim 6.

* * * * *

UNITED STATES PATENT AND TRADEMARK OFFICE
CERTIFICATE OF CORRECTION

PATENT NO. : 8,883,889 B2
APPLICATION NO. : 11/654154
DATED : November 11, 2014
INVENTOR(S) : Vincent Ruffieux et al.

It is certified that error appears in the above-identified patent and that said Letters Patent is hereby corrected as shown below:

In the Claims:

Col. 22, lines 45-47: "$R^{31}$, $R^{32}$, and $R^{33}$ independently of one another are hydrogen, carbamoyl, $C_{2-18}$-alkylcarbamoyl, $C_{2-18}$-alkoxycarborlyl" should read -- $R^{31}$, $R^{32}$, and $R^{33}$ independently of one another are hydrogen, carbamoyl, $C_{2-18}$-alkylcarbamoyl, $C_{2-18}$-alkoxycarbonyl --.

Signed and Sealed this
Third Day of March, 2015

Michelle K. Lee
*Deputy Director of the United States Patent and Trademark Office*